United States Patent [19]

Hoffman

[11] Patent Number: 5,054,584
[45] Date of Patent: Oct. 8, 1991

[54] LUBRICATING DEVICE FOR AIR DRIVEN DENTAL DRILLS

[76] Inventor: Elliott S. Hoffman, 5001 Desert Jewel Dr., Paradise Valley, Ariz. 85253

[21] Appl. No.: 586,684

[22] Filed: Sep. 24, 1990

[51] Int. Cl.[5] ............................................. F16N 7/30
[52] U.S. Cl. .................................. 184/55.1; 184/6.14; 184/105.3; 433/104
[58] Field of Search .................. 184/6.26, 6.14, 105.3, 184/55.2, 55.1, 105.1; 433/104

[56] References Cited

U.S. PATENT DOCUMENTS

| | | | |
|---|---|---|---|
| 827,519 | 7/1906 | Emery | 184/60 |
| 1,388,459 | 8/1921 | Greene et al. | 184/55.2 |
| 2,039,177 | 4/1936 | Kenzie | 433/92 |
| 2,124,831 | 7/1938 | Roos | 433/104 |
| 2,988,815 | 6/1961 | Staunt | 433/87 |
| 3,197,869 | 8/1965 | Staunt | 433/84 |
| 3,261,426 | 7/1966 | Kuhlman | 184/55.2 |
| 3,304,051 | 2/1967 | Calhoun | 415/80 |
| 3,879,851 | 4/1975 | Landgraf | 433/104 |
| 3,946,490 | 3/1976 | Sotman et al. | 433/82 |
| 3,977,083 | 8/1976 | Leslie et al. | 222/146.3 |
| 4,218,216 | 8/1980 | Sugai et al. | 433/104 |
| 4,490,113 | 12/1984 | Kawada | 433/104 |

FOREIGN PATENT DOCUMENTS 2526125  4/1982  France.

*Primary Examiner*—Ira S. Lazarus
*Assistant Examiner*—Alan B. Cariaso
*Attorney, Agent, or Firm*—Cahill, Sutton & Thomas

[57] ABSTRACT

A lubrication device for a dental drill having an air turbine motor, or like handpiece, includes a housing having air and water passage extending therein for coupling a flexible supply hose to the handpiece. A conduit extends from the housing and provides a lubrication passageway in fluid communication with the pressurized air inlet passageway leading to the air turbine motor. The conduit includes a cap releasably secured to the end of the conduit. The nozzle of a lubricant reservoir may be inserted within the conduit after temporarily removing the cap for permitting the nozzle to be advanced through the housing and into the handpiece for lubricating the air turbine motor. The device may be provided as an adapter for insertion between the handpiece and the supply hose. Alternately, the proximal end of the housing may be permanently secured to the end of the supply hose.

9 Claims, 2 Drawing Sheets

LUBRICATING DEVICE FOR AIR DRIVEN DENTAL DRILLS

FIELD OF THE INVENTION

This invention relates to dental drills, and more particularly, to apparatus for lubricating dental drills or other hand pieces having air turbine motors.

BACKGROUND OF THE INVENTION

Dental drills and similar handpieces often include an air powered turbine head containing a turbine rotor which must be lubricated each day. At present, such daily lubrication requires that the supply hose, which provides pressurized air and water, and in some instances, a source of light, to the dental drill, be uncoupled from the drill so that an elongated, flexible nozzle of a lubricant spray container can be inserted into the air inlet opening of the dental drill that leads to the turbine rotor; the lubricant, typically oil, is then sprayed into the turbine area of the drill. Following lubrication, the supply hose must be reattached to the drill. Reattachment of the supply hose to the dental drill is delicate, taxing, and time-consuming; therefore, personnel assigned the task of lubricating such dental drills often neglect it, and expensive turbines burn out faster than expected Those skilled in the art have attempted to solve the problem of easily and effectively lubricating dental drills but have not been entirely successful. U.S. Pat. No. 3,879,851 to Landgraf discloses a device for lubricating dental drills with aerosol spray containers without disassembly of the drills prior to lubrication. The patent to Landgraf discloses an intermediate piece coupled between the turbine head and a hand grip. The intermediate piece includes a port normally sealed by a ball valve whenever the drill is operated. The nozzle of a lubricant container may be introduced into the port when the drill is not in use. However, the nozzle may not be advanced to any significant degree into the drill itself; therefore, the lubricant is not efficiently directed toward the turbine head and can dissipate inside the intermediate piece before reaching the turbine head.

U.S. Pat. No. 3,946,490 to Sotman et al. discloses a device for aerosol lubrication of dental drills. The Sotman device is a specially designed dental handpiece which includes a lubrication opening ordinarily sealed by a sliding clip or collar. A lubrication opening projects angularly into the turbine housing. During lubrication, a tube extending from the discharge port of an aerosol lubricant can is inserted through the lubrication opening; therefore, lubricant can be injected directly from the lubricant can into the turbine housing. However, the Sotman device requires substantial modification to conventional dental drill handpieces which lack such opening.

U.S. Pat. No. 4,218,216 to Sugai et al. discloses a lubrication device inserted between the end of a dental handpiece and the flexible service hose for permitting lubricant to be added to the air supply line. Rather than permitting periodic application of a lubricant from an aerosol spray container, the device disclosed by Sugai et al. continuously adds a mist oil to the compressed air channel. However, such constant lubrication poses a significantly greater risk of inadvertently injecting such lubricant into a patient's mouth as compared with the practice of periodically lubricating a dental handpiece once each day.

In addition, French Patent No. 2526-125 discloses an air motor for a dental handpiece including an air inlet and a separate lubricant branch within the motor body connected to the air inlet passage. The lubricant branch houses a spring loaded, normally closed ball non-return valve. Oil is injected into the lubricant branch, forcing open the ball non-return valve by the pressure of the lubricating device. However, the air motor disclosed within this French patent would require substantial modification of dental handpieces that are already heavily in use.

Accordingly, it is an object of the present invention to provide a dental drill lubricating device for periodically lubricating dental drills without requiring disassembly of the dental drill from the associated supply hose.

It is another object of the present invention to provide such a dental drill lubricating device which can be used without modification of the dental handpiece itself.

It is still another object of the present invention to provide a dental drill lubricating device which permits the tip of the lubricant nozzle to be inserted into an air passage within the dental handpiece itself.

Other objects, advantages and features of the present invention will become more apparent from the following specification when taken in conjunction with the accompanying drawings.

SUMMARY OF THE INVENTION

Briefly described, and in accordance with preferred embodiments thereof, the present invention relates to a device for lubricating an air driven turbine rotor of a dental drill handpiece or the like, and including a housing having a distal end adapted to be connected to the proximal end of the handpiece. The housing includes an opposing proximal end adapted to be coupled to a supply hose. The housing includes at least an air inlet passage extending therethrough and providing a fluid connection from the supply hose to an air inlet passage of the handpiece. The lubricating device further includes a fastener for releasably fastening the distal end of the housing to the proximal end of the handpiece.

The lubricating device further includes a conduit which extends at an angle from the housing. The conduit has a first end secured to the housing in fluid connection with the air inlet passage extending therethrough. The conduit includes an opposing second end adapted to slidingly receive the flexible nozzle of a lubricant reservoir, such as an aerosol lubricant container. The conduit extends from its second end to its first end generally toward the distal end of the housing to convey the nozzle through the air inlet passage extending within the housing toward the turbine rotor. The lubrication passageway extending through the conduit forms a Y-junction with the air inlet passage extending through the housing to guide the tip of the lubricant nozzle into the handpiece.

A cap is releasably secured to the second end of the conduit to seal the opening therein between periods of lubrication. The cap may be releasably secured to the second end of the conduit through a threaded coupling or by a bayonet fitting.

The aforementioned fastener for releasably fastening the distal end of the housing to the proximal end of the handpiece preferably includes an internally threaded collar slidably engaged with the distal end of the housing and adapted to threadedly engage the proximal end of the handpiece.

In a first embodiment of the present invention, the device is provided in the form of an adapter for insertion between the handpiece and the supply hose. The proximal end of the housing has external threads formed upon the outer periphery thereof for being engaged by a second internally threaded collar slidably engaged with a terminal fitting of the supply hose.

In a second embodiment of the present invention, the housing of the lubrication device replaces the conventional terminal fitting of the supply hose, wherein the proximal end of the housing is substantially permanently secured to the grouping of bundled flexible passageways that form the supply hose.

DESCRIPTION OF THE PREFERRED EMBODIMENTS

Figure 1:
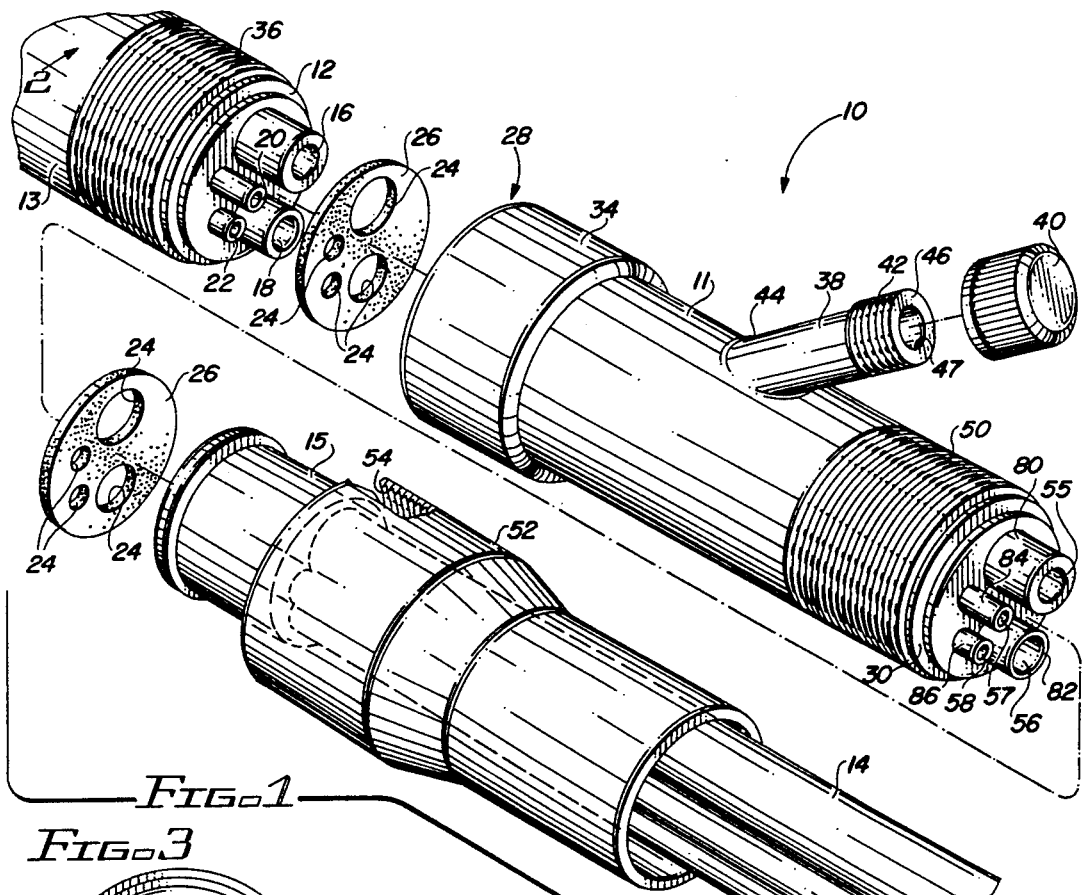
FIG. 1 is an expanded perspective view of a lubrication device of the present invention for attachment between a dental drill and a dental drill supply hose.

In FIG. 1, a first embodiment of a dental drill lubricating device is indicated generally by reference numeral 10. In this embodiment, device 10 is an intermediary coupler or adapter which can be used to retrofit to existing dental drills and associated supply hoses. Device 10 includes a generally cylindrical housing 11 having a distal end 28 and an opposing proximal end 30. Distal end 28 is adapted to be coupled to proximal end 12 of a handpiece 13 such as a dental drill; the opposing distal end (not shown) of handpiece 13 contains a turbine head including a turbine rotor to drive a tool such as a drill bit (not shown). Proximal end 30 of housing 11 is provided with male threads 50 upon the outer periphery thereof, and is adapted to abut and connect to terminal fitting 15 of supply hose 14. Preferably, the respective couplings of housing 11 to proximal end 12 of handpiece 13 and to terminal fitting 15 of supply hose 14 are sealed by placing one of a pair of rubber gaskets or grommets 26 between the handpiece end 12 and distal end 28 of housing 11, and between the supply hose terminal fitting 15 and proximal end 30 of housing 11.

Figure 3:
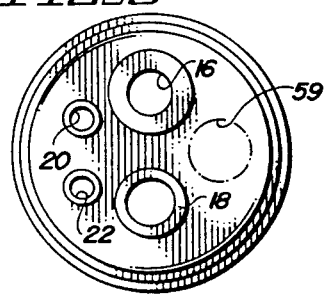
FIG. 3 is an end view of the lubrication device illustrated in FIGS. 1 and 2.

As shown most clearly in FIG. 3, handpiece end 12 include an enlarged pressurized-air inlet passage 16 and an air outlet passage 18 to circulate compressed, pressurized air from supply hose 14 to the turbine rotor and back; also shown in FIG. 3 is a water inlet passage 20 for admitting water that is directed at the site being drilled to cool the same. Another smaller inlet passage 22 is also shown in FIG. 3 to admit pressurized air which may be directed at the site being drilled to blow away debris. The various air and water inlet and outlet passages are accommodated by corresponding enlarged holes 24 in grommets 26. As shown in FIGS. 1 and 3, housing 11 contains corresponding air inlet and outlet passages 55 and 56, respectively, water inlet passage 57 and pressurized air passage 58; supply hose 14 contains a number of flexible passageways bundled together for conducting the flow of air and water between the handpiece and a source of compressed air and pressurized water. As shown in FIG. 3, an optional fiber optic port or passage 59 may also be included in handpiece 13, within housing 11, and within supply hose 14, to direct a light beam at the work area.

Figure 2:
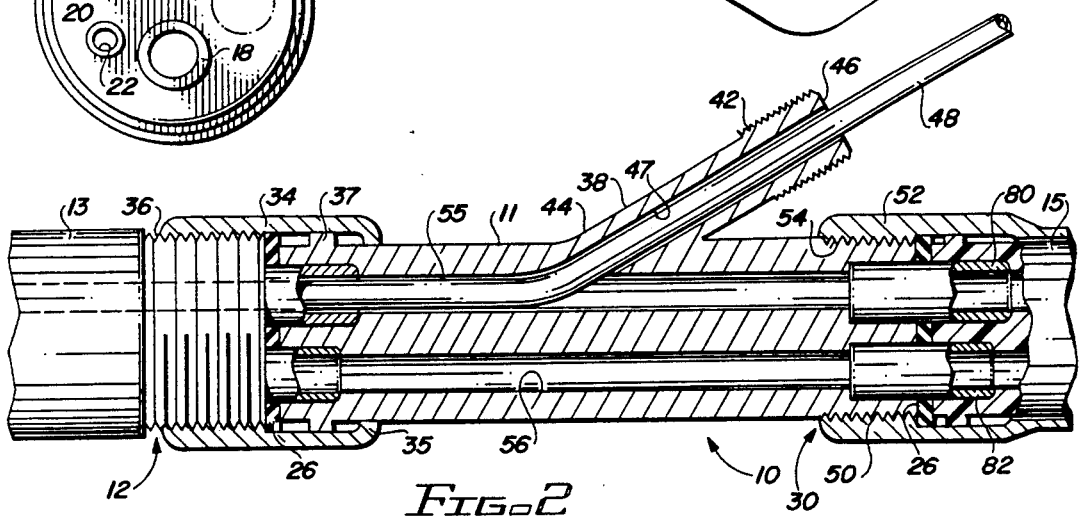
FIG. 2 is a sectional view of the lubrication device shown in FIG. 1 taken on lines 2—2 of FIG. 1.

As shown in FIGS. 1 and 2, a plurality of tubular fittings 80, 82, 84, and 86, each communicating with passages 55, 56, 57, and 58, respectively, within housing 11, extend from proximal end 30 of housing 11. Such tubular fittings extend through the corresponding apertures 24 within grommet 26. Tubular fittings 80–86 are received within correspondingly-sized sockets formed in terminal fitting 15 of supply hose 14. Preferably, tubular fittings 80–86 are of the same size and configuration as those extending from the proximal end of handpiece 13, whereby tubular fittings 80–86 readily mate with the sockets conventionally provided within terminal fitting 15. Thus, the proximal end of housing 11 is indistinguishable from the proximal end 12 of handpiece 13.

Referring generally to FIGS. 1 and 2, device 10 further includes a female internally-threaded collar 34 which fits around distal end 28 of housing 11; collar 34 is adapted to slide over distal end 28 of housing 11 and engage male threads 36 provided upon the outer periphery of proximal end 12 of handpiece 13. Before engaging collar 34 with proximal end 12, the air and water passages 16–22 projecting from handpiece 13 are inserted into the corresponding passages provided in the distal end 28 of housing 11. Collar 34 includes an inwardly-turned annular flange 35 adapted to engage an annular boss or ring 37 extending from distal end 28 of housing 11. When collar 34 is thereafter rotated and tightened on male threads 36, the annular flange of collar 34 urges boss 37 toward proximal end 12 of handpiece 13, compressing gasket 26. Device 10 thereby becomes locked to proximal end 12 of handpiece 13, with the various air and water passages of handpiece 13 and housing 11 properly aligned with each other, thus establishing fluid connections therebetween. Collar 34 therefore serves as a means to releasably fasten distal end 28 of housing 11 to proximal end 12 of handpiece 13.

Similarly, terminal fitting 15 of supply hose 14 includes a second slidable collar 52 slidably engaged with terminal fitting 15 and containing female internal threads 54, shown in FIG. 1, to engage male external threads 50 formed upon the outer periphery of proximal end 30 of housing 11. Collar 52 locks the proximal end 30 to terminal fitting 15 of supply hose 14, thus providing a fluid connection between the air and water passages within supply hose 14, and the corresponding air and water passages 55–58 of device 10.

Positioned approximately between distal end 28 and proximal end 30 of housing 11 and extending out at an angle therefrom is a tubular conduit 38. As shown in FIG. 2, first end 44 of conduit 38 is secured to housing 11 and is in fluid communication with air inlet passage 55 of housing 11. The second end 46 of conduit 38 opposite first end 44 has an outer periphery including male threads 42; a female threaded screw-on cap 40 is provided to fit over and releasably engage male threads 42, thus covering and sealing second end 46 of conduit 38 when lubrication is not being performed. As shown in FIG. 2, conduit 38 extends from second end 46 to first end 44 generally toward distal end 28 of housing 11. Conduit 38 provides a lubrication passageway 47 which forms a Y-junction with air inlet passageway 55 of housing 11 and which is adapted to slidingly receive therein a nozzle of a lubricant reservoir.

To lubricate the handpiece or drill 13, cap 40 is removed from second end 46 of conduit 38, and nozzle 48 of an oil spray container (not shown) is inserted into conduit 38 through second end 46 thereof, as shown in FIG. 2. The tip of nozzle 48 is advanced through passageway 47 and through air inlet passage 55 of housing 11, and further into air inlet passage 16 of handpiece 13 toward the vicinity of the turbine rotor (not shown). As shown in FIG. 2, the tip of nozzle 48 lies in a substantially coaxial relationship with air inlet passage 16 of handpiece 13. Oil is then sprayed from the oil container through nozzle 48 and up into the handpiece 13 to lubricate the turbine rotor.

Figure 4:
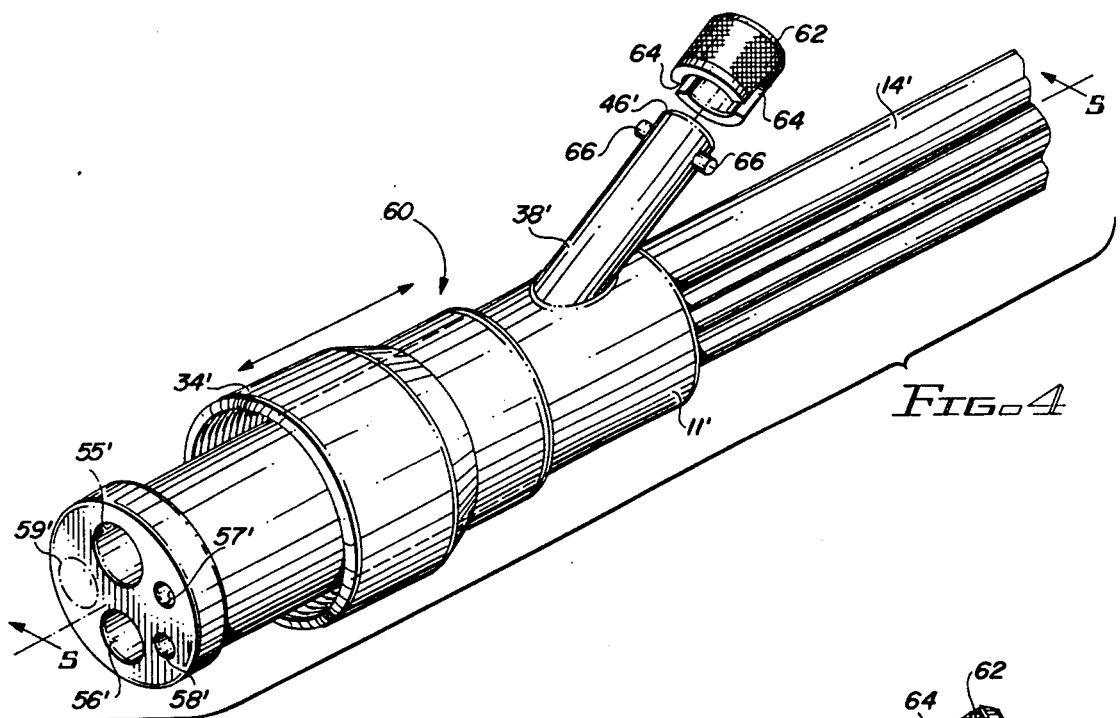
FIG. 4 is a perspective view of a second embodiment of the dental drill lubricating device of the present invention including modifications to the end of the dental supply hose.
Figure 5:
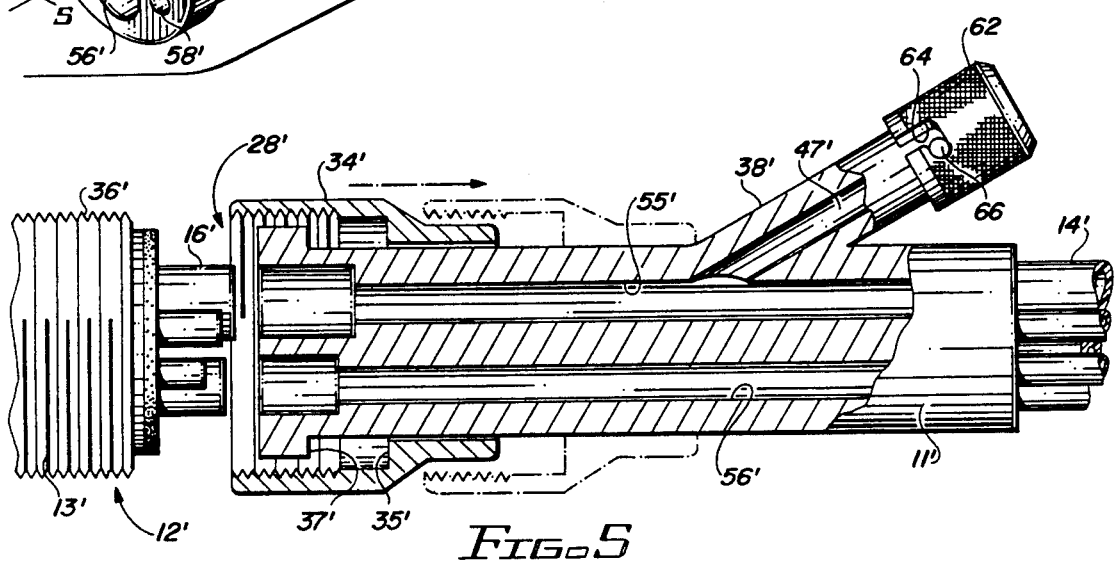
FIG. 5 is a sectional view of the lubrication device shown in FIG. 4 taken on lines 5—5 of FIG. 4.

A second embodiment of the dental drill lubricating device of the present invention is designated generally by reference numeral 60 in FIGS. 4 and 5. This embodiment is intended to be incorporated within newly manufactured supply hoses for dental drills or similar handpieces. Many of the elements of this embodiment are similar to those described with respect to the embodiment illustrated in FIGS. 1-3; therefore, those elements within FIGS. 4 and 5 which correspond with those already identified in FIGS. 1-3 are designated by like reference numerals. The major difference is that device 60 is intended to be permanently connected to supply hose 14', in substitution for terminal fitting 15, thereby eliminating the need for a separate adapter or coupler between supply hose 14' and handpiece 13'. Another difference is that second end 46' of conduit 38' is covered by a bayonet type cap 62 having a pair of opposing L-shaped slots 64 adapted to receive and releasably engage pins 66 extending from the outer surface of conduit 38' adjacent second end 46'. As with the embodiment described with respect to FIGS. 1-3, the nozzle of a spray oil container can be inserted into second end 46' of conduit 38', advanced through lubrication passage 47' of conduit 38' into air inlet passage 55' of housing 11', and thence into the air inlet passage 16' of handpiece 13' toward the air turbine to lubricate the turbine rotor.

Figure 6:
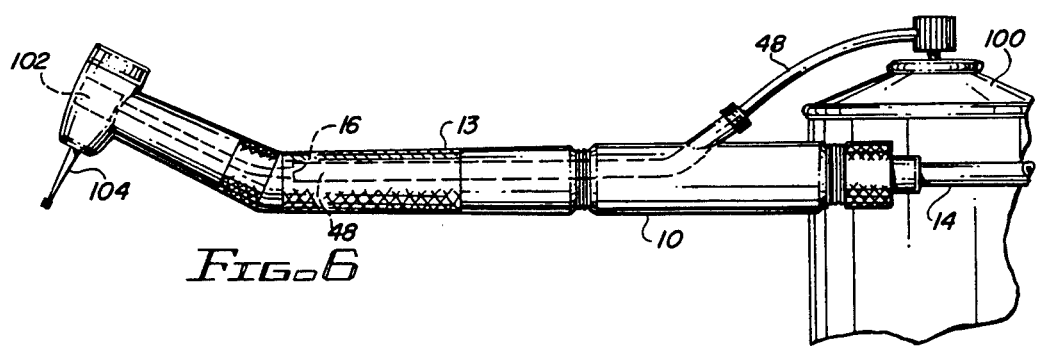
FIG. 6 is a side view of the present lubrication device coupled between a supply hose and a dental handpiece and being used to lubricate the turbine head of the dental handpiece.

Within FIG. 6, lubrication device 10 is shown coupled between dental handpiece 13 and supply hose 14. As shown in FIG. 6, dental handpiece 13 includes a turbine rotor 102 for rotating a tool 104 such as a drill bit. Also shown in FIG. 6 is a lubricant reservoir in the form of an oil spray container 100 having nozzle 48. Nozzle 48 extends within conduit 38, and into air inlet passage 16 of dental handpiece 13.

While the present invention has been described in accordance with two preferred embodiments thereof, the description is for illustrative purposes only and should not be construed as limiting the scope of the invention. Various changes and modifications may be made by those skilled in the art without departing from the true spirit and scope of the invention as defined by the appended claims.

I claim:

1. A device for lubricating an air driven turbine rotor of a dental drill handpiece or the like, the handpiece having a proximal end providing at least an air inlet passage for supplying pressurized air to the turbine rotor, and having an opposing distal end for rotating a tool, said device comprising:
   a) a housing having a distal end adapted to be connected to the proximal end of the handpiece, and having an opposing proximal end adapted to be coupled to a supply hose, the housing having at least an air inlet passage extending therethrough and providing a fluid connection from the supply hose to the air inlet passage of the handpiece;
   b) fastening means for releasably fastening the distal end of said housing to the proximal end of the handpiece;
   c) a conduit extending at an angle from the housing, said conduit having a first end secured to said housing between the distal and proximal ends thereof, the first end of said conduit being in fluid connection with the air inlet passage of said housing, said conduit having an opposing second end adapted to slidingly receive therein a nozzle of a lubricant reservoir, the nozzle having a tip;
   d) a cap releasably secured to the second end of said conduit to seal the second end of said conduit when the nozzle is not received therein; and
   e) said conduit being generally direct toward the distal end of said housing to convey the tip of the nozzle through the housing toward the turbine rotor, and to guide the tip of the nozzle into a coaxial relationship with the air inlet passage of the handpiece, whereby lubricant can be supplied from the lubricant reservoir through the nozzle toward the turbine rotor.

2. A device as recited by claim 1 wherein the proximal end of the handpiece includes external threads upon the outer periphery thereof, said fastening means including an internally threaded collar slidably engaged with the distal end of said housing and adapted to threadedly engage the externally threaded proximal end of the handpiece to releasably secure the distal end of the housing to the proximal end of the handpiece, with the air inlet passage of the handpiece and the air inlet passage of the housing being in fluid communication with each other.

3. A device as recited by claim 2 wherein the supply hose terminates in a fitting having at least an air inlet passage therein and including a second collar slidably engaged with the terminal fitting, the second collar being internally threaded, and the proximal end of said housing having external threads formed upon the outer periphery thereof for being engaged by the second collar for joining the proximal end of said housing with the terminal fitting of the supply hose.

4. A device as recited by claim 1 wherein the second end of said conduit is threaded, and wherein said cap is also threaded to releasably engage the second end of said conduit.

5. A device as recited by claim 1 wherein a pair of pins project in opposing directions from the second end of said conduit, and wherein said cap includes a pair of corresponding L-shaped slots for receiving said pins and forming a releasable bayonet-type fitting between said cap and the second end of said conduit.

6. The device as recited by claim 1 wherein the supply hose includes a plurality of bundled flexible passageways for conducting the flow of air and water, and wherein said housing includes a corresponding plurality of passageways for conducting the flow of air and water between the supply hose and the handpiece.

7. The device as recited by claim 6 wherein the proximal end of said housing is substantially permanently secured to the supply hose.

8. A device as recited by claim 3 wherein a plurality of tubular fittings extend from the proximal end of said housing, said tubular fittings being in fluid communication with a corresponding plurality of passageways within said housing, said device further including a grommet having apertures formed therein, the apertures corresponding in size and number to the plurality of tubular fittings extending from the proximal end of said housing, said plurality of tubular fittings extending through the corresponding apertures of said grommet, and said grommet sealing the proximal end of said housing to the terminal fitting of the supply hose.

9. A device as recited by claim 1 wherein said conduit includes a lubrication passageway in fluid communication with the air inlet passage of said housing, said lubrication passageway forming a Y-junction with the air inlet passageway provided within said housing.

* * * * *